United States Patent [19]

March

[11] Patent Number: 6,034,605
[45] Date of Patent: Mar. 7, 2000

[54] SYSTEM/METHOD FOR SECURE STORAGE OF PERSONAL INFORMATION AND FOR BROADCAST OF THE PERSONAL INFORMATION AT A TIME OF EMERGENCY

[76] Inventor: Anthony W. March, 202 Par Dr., Williamsburg, Va. 23188

[21] Appl. No.: 09/207,641

[22] Filed: Dec. 8, 1998

[51] Int. Cl.[7] .................................................. G08B 23/00
[52] U.S. Cl. .............................. 340/573.1; 340/825.31; 340/825.34; 128/690; 379/38; 379/45; 705/3
[58] Field of Search ........................... 340/573.1, 825.34, 340/825.31; 128/690; 379/38, 45; 342/357, 457; 705/3

[56] References Cited

U.S. PATENT DOCUMENTS 5,825,283  10/1998  Camhi ..................................... 340/438
5,955,952   9/1999  Bergman et al. ..................... 340/573.1

Primary Examiner—Benjamin C. Lee
Attorney, Agent, or Firm—Peter J. Van Bergen

[57] ABSTRACT

A method and system are provided for storing an individual's personal information and for broadcast thereof at a time of emergency. A sealed package contains a medium storing personal information associated with an individual. The sealed package is stored at a facility until an emergency occurs. At a time of emergency, a missing person report concerning the individual generated by a law enforcement agency is processed. The personal information in the individual's sealed package is accessed in response to the missing person report and then broadcast on an electronic bulletin board accessible via the internet.

26 Claims, 3 Drawing Sheets

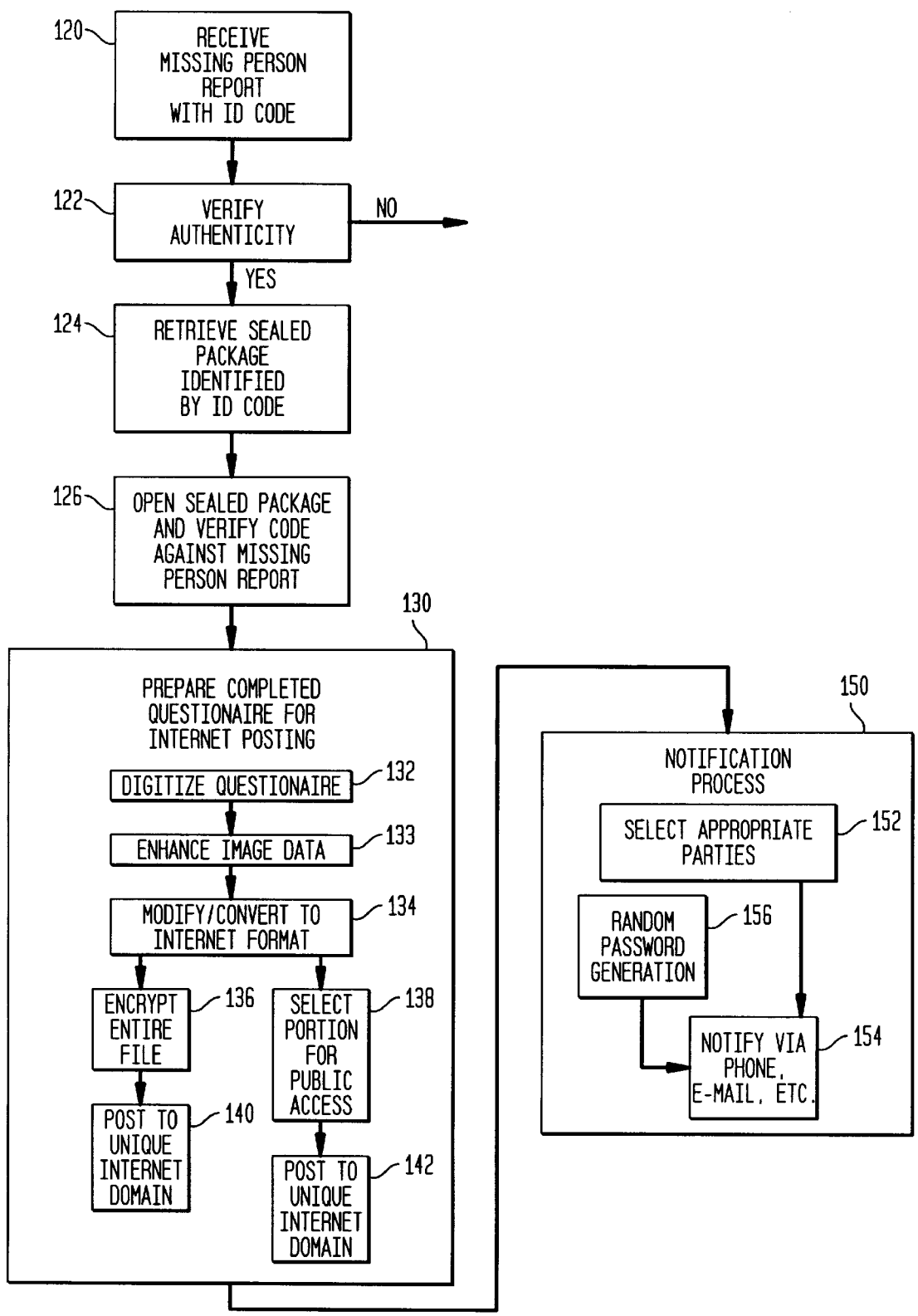

SYSTEM/METHOD FOR SECURE STORAGE OF PERSONAL INFORMATION AND FOR BROADCAST OF THE PERSONAL INFORMATION AT A TIME OF EMERGENCY

FIELD OF THE INVENTION

The invention relates generally to methods and systems that facilitate the search for missing persons, and more particularly to a system and method that provides for the secure storage of personal information and for broadcast of the personal information at a time of emergency to aid in search operations.

BACKGROUND OF THE INVENTION

Law enforcement agencies know that the minutes and hours immediately after a child or other person is reported lost or missing are critical to a successful search operation. It is during this time that information about the missing person can be most effectively used by both law enforcement and other searching individuals and/or organizations. It is during this time that the missing person is most likely to be near his or her "last seen" location. Unfortunately, it is also during this time that the missing person's loved ones, e.g., parents, legal guardian, etc., are experiencing one of the most traumatic events of their lives. Thus, their ability to provide relevant information about the missing person is greatly inhibited by the emotion of the moment. Further, information that law enforcement needs about the missing person may not be readily or otherwise accessible.

SUMMARY OF THE INVENTION

Accordingly, it is an object of the present invention to provide a method and system that can facilitate the search for a missing person.

Another object of the present invention is to provide a method and system that allows a parent or other legal guardian to provide law enforcement with critical personal information about a missing child or other loved one during a time of emergency.

Still another object of the present invention is to provide a method and system that quickly disseminates critical personal information about a missing person to law enforcement agencies, the media and other organizations that participate in search operations.

Other objects and advantages of the present invention will become more obvious hereinafter in the specification and drawings.

In accordance with the present invention, a method and system are provided for storage of an individual's personal information and for broadcast thereof at a time of emergency in order to facilitate a search for the individual. A sealed package contains a medium storing personal information associated with an individual. The sealed package is stored at a facility until an emergency occurs. At a time of emergency, a missing person report concerning the individual generated by a law enforcement agency is processed. The personal information in the individual's sealed package is accessed in response to the missing person report. The personal information associated with the individual identified in the missing person report is then broadcast on an electronic bulletin board accessible via the internet. A portion of an individual's personal information will be available to the general public at one internet domain site. However, the entirety of an individual's personal information will be encrypted and made available at a second secure internet domain site accessible only to those parties having a uniquely assigned password.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein:

FIG. 3 is a flow chart of the broadcast portion of the method of the present invention.

DETAILED DESCRIPTION OF THE INVENTION

Figure 1:
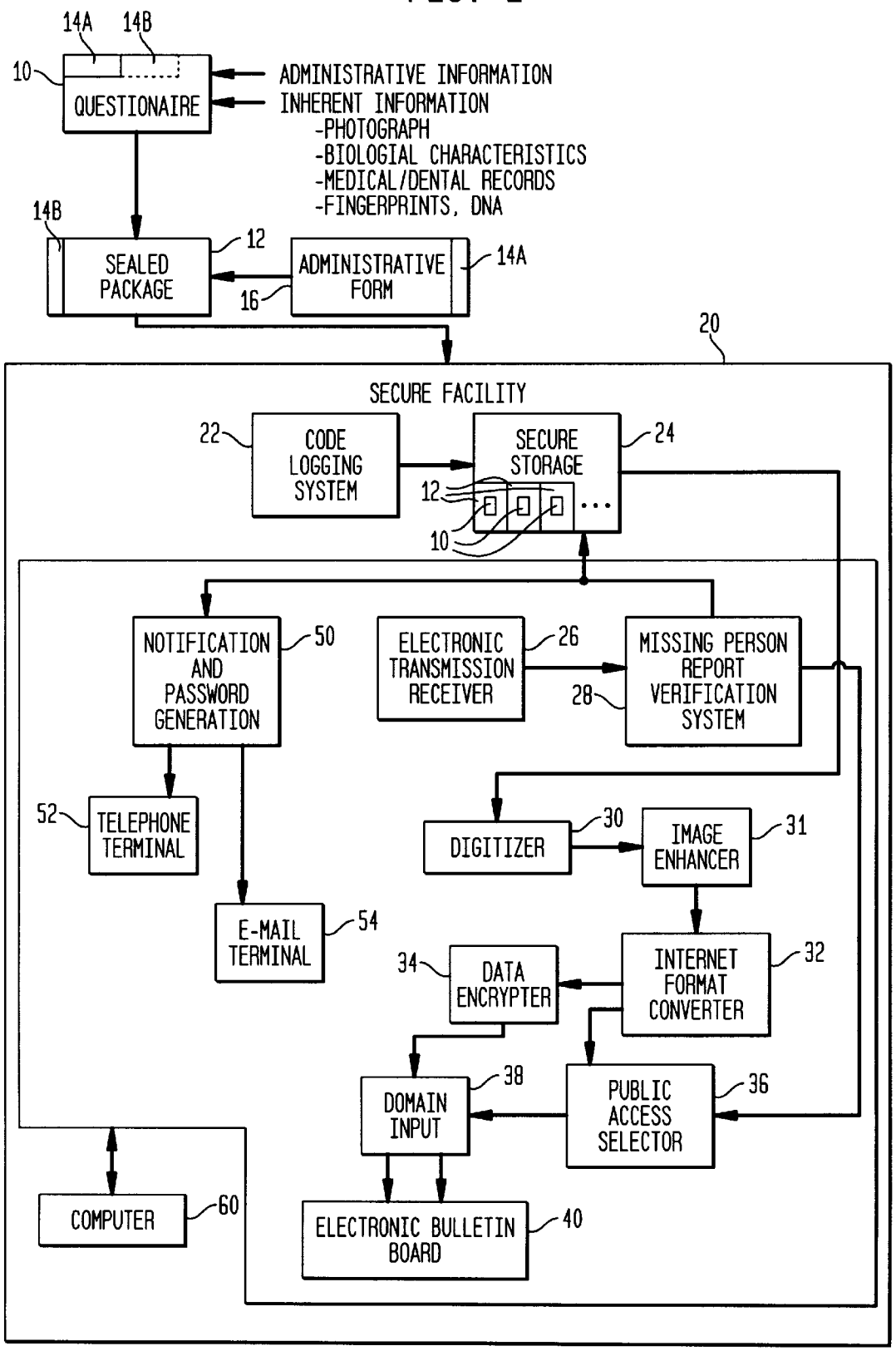
FIG. 1 is a block diagram of a system overview of the present invention.
Figure 2:
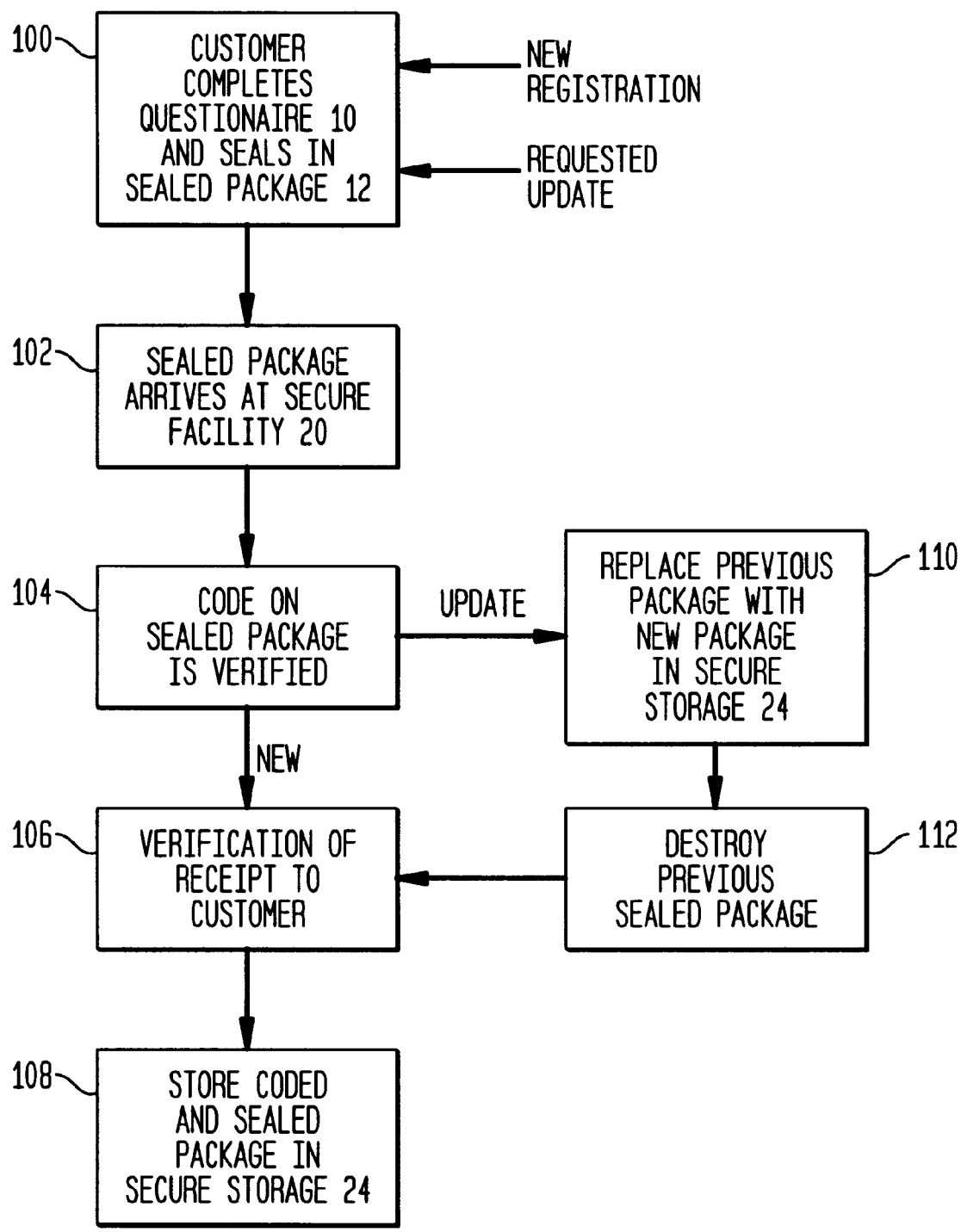
FIG. 2 is a flow chart of the registration and information storage portions of the method of the present invention.

Referring now to the drawings, FIG. 1 depicts a system overview of the present invention is illustrated in block diagram form, and FIGS. 2 and 3 are flow charts of the steps involved in the method of the present invention. By way of example, the present invention will be described for its use in facilitating the search for a missing or lost child. However, it is to be understood that the present invention can be used to facilitate the search for any individual that has been reported missing.

In general, the present invention provides for the storage of personal information associated with an individual and, if ever necessary, provides for the broadcast of the personal information in order to facilitate a search for the individual. In terms of storage of the personal information, a data questionnaire 10 is supplied to the individual or, in the case of a child or incompetent individual, to the child's parent(s) or other legal guardian. Questionnaire 10 can take the form of standardized printed forms that ask for both administrative and inherent information associated with the individual. Administrative information can include, but is not limited to, name and address, social security number, school information, parent and grandparent information, custodial rights information, etc. Inherent information can include, but is not limited to, appearance information such as photographs, hair/eye color, identifying birth marks, body piercing, etc; distinguishing medical conditions of both the visually apparent and visually imperceptible variety; and innate distinguishing characteristics, such as fingerprints, DNA, etc. When questionnaire 10 is complete, it is placed in a package 12 and sealed therein. To ensure the integrity of questionnaire 10, sealed package 12 is typically made of a non-tearable waterproof material. Sealed package 12 contains only information associated with one individual.

Each questionnaire 10 and sealed package 12 are coded with a unique identification code that will be supplied to law enforcement at a time of emergency. While this can be accomplished in a variety of ways, one method will be described by way of example. Questionnaire 10 can be precoded with a unique identification code in the form of a numeric code, an alphanumeric code and/or a machine-readable representation thereof, e.g., bar code, matrix code, etc. The identification code is integral with questionnaire 10 at 14A and is repeated identically in a removable form (e.g., sticker) at 14B as indicated by the dotted line designation. Before closing sealed package 12, removable code 14B is removed from questionnaire 10 and affixed to sealed package 12. Sealed package 12 is then forwarded with an administrative form 16 to secure facility 20. Administrative form 16 identifies the person (e.g., name, address, social security number, etc.) whose information is contained in sealed package 12. Note that identification code 14A can also be integrated into/onto administrative form 16. Similarly, rather than using a removable code 14B, sealed package 12 can have the identification code integrated therein/thereon as is the case with administrative form 16. The customer will retain a copy of the unique identification code in the form of, for example, an identification card or tag.

Sealed package 12 is delivered to a secure facility 20 which can be one central location or several regional locations linked to one another for information sharing purposes. Secure facility 20 can include a code logging system 22 that logs each unique identification code for each sealed package 12 received. Code logging system 22 can include apparatus for appropriately reading and verifying that the identification code on sealed package 12 matches that on the accompanying administrative form 16. A secure storage 24, e.g., vault, is provided to warehouse each sealed package 12 that has been logged. As will be explained further below, a sealed package 12 remains in storage 24 until either an emergency occurs, updated information about the individual is provided by way of a new sealed package containing the updated information, or a verifiable request is made to destroy the individual's sealed package due to death or a desire to no longer be registered in accordance with the present invention.

Secure facility 20 is equipped to process missing person reports generated by a law enforcement agency. For speed and efficiency, an electronic transmission receiver(s) 26, e.g., dedicated FAX machine(s), personal computers incorporating FAX capability, etc., are maintained and monitored 24 hours a day. Monitoring can be human and/or machine implemented at a verification system 28 which verifies the authenticity of a received missing person report.

An authenticated missing person report triggers the access and opening of a particular sealed package 12 from secure storage 24 associated with the individual identified in the missing person report. After verifying that the identification code supplied with the missing person report matches that on sealed package 12 and on questionnaire 10 contained therein, the associated questionnaire 10 is converted to a digital data file at digitizer 30. When questionnaire 10 is implemented by means of data forms, an optical scanner can be used for digitizer 30. Note that if questionnaire 10 is already in a digital data format, digitizer 30 is not required. The digital data file should be one that can be reproduced as an image.

The digital image data file can be processed at image enhancer 31 such that an image reproduced therefrom would be enhanced. That is, image enhancer 31 represents well known image processing systems and methods that improve image color, contrast and/or clarity. The enhanced image data is then prepared for internet posting in the present invention by first formatting the file at internet format converter 32. Specifically, typical image data formats (e.g., ".jpg", ".btmp", etc.) are converted to standard internet language codes such as HTP, HTML and/or VRML. Such formatting techniques are well known in the art and will therefore not be described herein. The entire formatted file is encrypted at data encrypter 34. As will be explained further below, a portion of the formatted file is selected for public access at selection module 36. Module 36 could be realized by a processor programmed to automatically select just certain data forms or parts thereof from the completed questionnaire suitable for public access, e.g., name, address, photographs. Additionally, module 36 could receive "last seen" information from verification system 28. A domain input module 38 is provided to assign/post the encrypted data and the unencrypted data to an electronic bulletin board 40 which can have its server based at secure facility 20. Bulletin board 40 defines a world wide web site that is accessible via the internet while each assigned domain defines a page at the world wide web site.

Secure facility 20 is also equipped to notify a large number of parties, e.g., federal/state/local police, media, etc., once the encrypted and unencrypted data has been posted to bulletin board 40. A notification and password generation module 50 generates random and unique passwords for selected parties that will be permitted to access the encrypted data. The selected unencrypted portion of an individuals personal information would be generally accessible on the internet. Notification of the selected parties occurs by using telephone terminals 52 or electronic mail (e-mail) terminals 54. Terminals 52 and/or 54 could be operated manually or automatically as controlled by a computer 60.

Similarly, control of other systems just described could be automated by computer 60. For example, verification system 28 could be programmed to verify that an incoming missing person report was transmitted from a law enforcement agency. This could be accomplished by linking a "caller id" system with a database of authentic origination telephone numbers. Further verification could be achieved by automatically calling the law enforcement agency and requesting a verification code which could be input from a telephone's keypad. Computer 60 could also control automatic storage/retrieval of sealed package 12 into/from secure storage 24. Once retrieved, sealed package 12 could be automatically opened and questionnaire 10 removed for input to digitizer 30.

The method of the present invention will now be explained with the aid of FIGS. 2 and 3. The first part of the method depicted in FIG. 2 involves the registration or storage of one's personal information. The second part of the method depicted in FIG. 3 involves the broadcast of the personal information in the event of an emergency, e.g., the person is missing. At step 100 in FIG. 2, a customer (e.g., the individual registering, a parent, guardian, etc.) completes a questionnaire 10 and seals same in a sealed package 12 with, if applicable, the removable form of the identification code being applied thereto. This is done when a person is being registered for the first time or in response to request for updated information. In terms of children, it is recommended that personal information be updated annually or if some substantial change has taken place, e.g., address change, custodial change, new medical condition, etc. At step 102, sealed package 12 arrives at secure facility 20. Whether containing new or updated personal information, sealed package 12 has its code verified against that on the accompanying administrative form 16 at step 104. If this is a new registration, verification of receipt of the sealed package can be provided to the customer at step 106. A new registration is then immediately stored in secure facility 24 at step 108. However, if the sealed package contains updated personal information, the previous sealed package (associated with the particular individual) is replaced with the new sealed package in secure facility 24 at step 110. At step 112, the previous sealed package and its contents are destroyed. Once again, verification can be provided to the customer at step 106. This completes the first part of the present method as it relates to registration and storage of an individual's personal information.

The second part of the present invention relates to the broadcast of an individual's personal information at a time of emergency. When an individual has been reported as "missing" to law enforcement, a missing person report is generated. At that time, the unique identification code (provided on questionnaire 10) is given to the law enforcement officials for inclusion in the missing person report. The missing person report and identification code are sent (e.g., via FAX or other electronic transmission) to secure facility 20. Once received at step 120, the missing person report is verified at step 122. Verification could be accomplished by manually or automatically phoning the originating law enforcement agency for a verbal verification and/or electronically generated (e.g., telephone keypad generated tones) code verification.

A verified missing person report triggers access or retrieval (at step 124) of the sealed package identified by the identification code on the missing person report. The retrieved sealed package is opened at step 126 and its identification code is verified against that supplied in the missing person report. After verifying that the identification code supplied with the missing person report matches that on sealed package 12 and on questionnaire 10 contained therein, the completed questionnaire is prepared at step 130 for posting on the internet.

The pre-posting procedure at step 130 begins with digitizing of the personal information contained in the completed questionnaire at step 132. For example, an optical scanner could be used at step 132 if paper data forms were used for the questionnaire. However, if the personal information is already digitized, e.g., stored on a disk or CD, step 132 could be eliminated. In either case, the digital data provided to step 133 should be reproducible as an image. At step 133, the image data can be enhanced to improve image color, contrast, clarity, etc.

As discussed above, most image data is in a format that is not compatible with formats used by the internet. Accordingly, the image data must be modified/converted at step 134 to be compatible with the internet using techniques well known in the art. In most instances, the compatible format is HTML.

Recognizing that some of an individual's personal information is very private but critical to a search operation, the present invention broadcasts only certain information publicly and restricts access to the entirety of the personal information. Accordingly, the entirety of the properly formatted data (i.e., all of the individual's personal information to include that which is private) is encrypted at step 136. Such encryption includes coding that requires a password to unencrypt the data. The particular encryption software used can be selected from those commercially available. The encrypted data is assigned/posted to a unique internet domain at step 140. Only those individuals/organizations with a valid password are able to access the encrypted data at the assigned internet domain. As mentioned above, a portion of an individual's personal information is made available for public access. The public access portion is selected at step 138 and assigned/posted to another unique internet domain at step 142.

Posting of an individual's personal information triggers a notification process step 150. Specifically, a number of appropriate parties are selected at step 152 for immediate notification. For example, in the case of a missing child, selected parties could include the reporting police department and surrounding area police departments, state police, the Federal Bureau of Investigation, local and state governing officials, local/state/national volunteer groups and centers, local and national media, etc. The particular selected parties can vary depending on the particular individual that is missing and the circumstances. Further, the particular parties permitted access to the encrypted data will vary depending on the circumstances. Once selected, the parties are immediately notified at step 154 via telephone and/or e-mail communication. As mentioned above, such notification could be accomplished using personnel and/or a computer-controlled message delivery system. For those parties that are to be permitted access to the encrypted data, a random password is generated at step 156. Each random password generated is unique for each selected party each time an individual's information has been posted. In this way, access to sensitive information is always limited to a "need to know" basis.

The advantages of the present invention are numerous. Precious time immediately following the report of a missing person is put to the best use possible. The internet broadcast of an individual's personal information means that law enforcement and other organizations can begin their search immediately and have all pertinent information at their fingertips. The color and resolution made possible by broadcast of enhanced image data on the internet means that crucial photographic information is of the highest quality and is readily accessible by all relevant parties. Previously, law enforcement would rely on FAX transmissions which do not provide good image clarity and definition.

The use of limited access and public access internet domains means that crucial search information can be made available while still maintaining an individual's privacy as it relates to sensitive information. Further, since the personal information was assembled systematically rather than at a time of extreme emotional trauma, the chances of forgetting important identification information is eliminated.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A system for storage of an individual's personal information and for broadcast thereof at a time of emergency to facilitate a search for said individual, said system comprising:

a sealed package containing a medium storing personal information associated with an individual;

a facility for storing said sealed package;

means for processing a missing person report concerning said individual, said missing person report having been generated by a law enforcement agency;

an electronic bulletin board accessible via the internet;

means for accessing said personal information only in response to said missing person report; and means for broadcasting said personal information associated with said individual on said electronic bulletin board only in response to said missing person report.

2. A system as in claim 1 wherein said personal information includes inherent information specific to said individual.

3. A system as in claim 2 wherein said inherent information includes visually discernible biological information specific to said individual.

4. A system as in claim 2 wherein said inherent information is visually imperceptible information specific to said individual.

5. A system as in claim 4 wherein said inherent information includes DNA information on said individual.

6. A system as in claim 4 wherein said inherent information includes fingerprints of said individual.

7. A system as in claim 2 wherein said inherent information includes photographic information of said individual.

8. A system as in claim 1 wherein said personal information includes custodial rights information specific to said individual.

9. A system as in claim 1 further comprising means for notifying a plurality of parties when said personal information has been broadcast on said electronic bulletin board.

10. A system as in claim 9 wherein said means for notifying includes a telephonic transmission device.

11. A system as in claim 9 wherein said means for notifying includes an electronic mail transmission device.

12. A system as in claim 1 wherein said medium comprises data forms.

13. A system as in claim 1 wherein said means for processing comprises:
   means for receiving an electronically transmitted version of said missing person report; and
   means for verifying authenticity of said missing person report.

14. A system as in claim 1 wherein said means for broadcasting comprises:
   a digitizer for converting said personal information into digital data that can be reproduced as an image;
   means for converting said digitized data into formatted data having a format that is compatible with the internet;
   means for encrypting said formatted data wherein encrypted formatted data is formed; and
   means for posting said encrypted formatted data to a first internet domain and for posting a portion of said formatted data to a second internet domain.

15. A system as in claim 14 further comprising means for processing said digital data from said digitizer wherein said image reproducible therefrom is enhanced.

16. A system as in claim 14 further comprising means for notifying a plurality of parties when said encrypted formatted data has been posted to said first internet domain and for supplying each of said plurality of parties with a unique password required for gaining internet access to said encrypted formatted data associated with said individual.

17. A method for storage of an individual's personal information and for broadcast thereof at a time of emergency to facilitate a search for said individual, said method comprising the steps of:
   receiving, at a secure facility, a medium in a sealed package, said medium storing personal information associated with an individual;
   storing said sealed package in said secure facility;
   processing a missing person report concerning said individual, said missing person report having been generated by a law enforcement agency;
   accessing said personal information in response to a missing report;
   providing an electronic bulletin board accessible via the internet; and
   broadcasting said personal information associated with said individual on said electronic bulletin board only in response to said missing person report.

18. A method according to claim 17 further comprising the step of coding said sealed package with a unique identifying code prior to said step of receiving.

19. A method according to claim 17 further comprising the steps of:
   receiving a subsequent sealed package at said secure facility, said subsequent sealed package containing another medium storing updated personal information associated with said individual; and
   replacing said sealed package with said subsequent sealed package wherein said subsequent sealed package is made available for said step of opening and said updated personal information is made available for said step of broadcasting.

20. A method according to claim 19 further comprising the step of destroying said sealed package along with said medium contained therein.

21. A method according to claim 19 further comprising the step of requesting said updated personal information associated with said individual on a periodic basis.

22. A method according to claim 17 wherein said step of processing comprises the steps of:
   receiving an electronically transmitted version of said missing person report; and
   verifying authenticity of said missing person report.

23. A method according to claim 17 wherein said step of broadcasting comprises the steps of:
   converting said personal information into digital data that can be reproduced as an image;
   converting said digitized data into formatted data having a format that is compatible with the internet;
   encrypting said formatted data wherein encrypted formatted data is formed; and
   posting said encrypted formatted data to a first internet domain and for posting a portion of said formatted data to a second internet domain.

24. A method according to claim 23 further comprising the step of processing said digital data wherein said image reproducible therefrom is enhanced.

25. A according to claim 23 further comprising the steps of:
   notifying a plurality of parties when said encrypted formatted data has been posted to said first internet domain; and
   supplying each of said plurality of parties with a unique password required for gaining internet access to said encrypted formatted data associated with said individual.

26. A method according to claim 25 wherein each said unique password is randomly selected.

* * * * *